(12) United States Patent
Sayre et al.

(10) Patent No.: US 6,932,980 B1
(45) Date of Patent: Aug. 23, 2005

(54) METHOD OF MAKING MICROALGAL-BASED ANIMAL FOODSTUFF SUPPLEMENTS, MICROALGAL-SUPPLEMENTED ANIMAL FOODSTUFFS AND METHOD OF ANIMAL NUTRITION

(76) Inventors: Richard Sayre, 528 Park Blvd., Worthington, OH (US) 43085; Richard Wagner, 3416 Ashwood Dr., Bloomington, IN (US) 47401

( * ) Notice: Subject to any disclaimer, the term of this patent is extended or adjusted under 35 U.S.C. 154(b) by 423 days.

(21) Appl. No.: 09/765,142

(22) Filed: Jan. 18, 2001

(51) Int. Cl.[7] .......................... A23K 1/165; A23K 1/17
(52) U.S. Cl. .................. 424/442; 424/400; 424/439; 424/93.1; 424/93.2; 424/195.17
(58) Field of Search ......................... 424/400, 439, 424/442, 489, 93.1, 93.2, 93.7, 195.17, 1.17

(56) References Cited

U.S. PATENT DOCUMENTS

| | | | |
|---|---|---|---|
| 4,992,207 A | * 2/1991 | Darnall et al. | 516/101 |
| 5,670,191 A | 9/1997 | Cummings et al. | 426/2 |
| 5,686,125 A | 11/1997 | Mueller | 426/74 |

FOREIGN PATENT DOCUMENTS

| | | |
|---|---|---|
| WO | 99/60838 | 12/1999 |

OTHER PUBLICATIONS

Brown, S., Metal–Recognition by Repeating Polypeptides, Nature Biotechnology 15: 269–272 (1997).

Harford, C. et al., Amino Terminal Cu(II)– and Ni(II)–Binding (ACTCUN) Motif of Proteins and Peptides: Metal Binding, DNA Cleavage, and Other Properties, Acc. Chem.

Kotrba, P. et al., Enhanced Bioaccumulation of Heavy Metal Ions by Bacterial Cells Due to Surface Display of Short Metal Binding Peptides, Applied and Enivornmental Microbiology 65: 1092–1098 (1999).

Nucifora, G. et al., Cadmium Resistance from *Staphylococcus aureus* Plasmid pI258 cadA Gene Results from a Cadmium–Efflux ATPase, Proc. Nat. Acad. Sci. 86: 3544–3548 (1989).

(Continued)

*Primary Examiner*—Thurman K. Page
*Assistant Examiner*—Charesse Evans
(74) *Attorney, Agent, or Firm*—Standley Law Group LLP

(57) ABSTRACT

The present invention is to a safe, biodegradable trace metal binding system that effectively delivers chromium, cobalt, copper, iron, manganese, molybdenum, selenium and zinc to animals. The method of preparing an animal foodstuff composition involves the steps of: providing transgenic algal cells comprising a nucleotide sequence, the nucleotide sequence being capable of expressing a non-native metal-binding protein in the transgenic algal cells; binding the metal-binding protein with at least one metal so as to produce a metal-bound adduct of the metal-binding protein; and admixing the metal-bound adduct with animal foodstuff. The invention is also to a animal foodstuff composition comprising animal foodstuff and transgenic algal cells expressing a non-native metal-binding protein in the transgenic algal cells, such that the transgenic algal cells contain the metal-binding protein and the metal-binding protein being bound to a metal.

13 Claims, 1 Drawing Sheet

OTHER PUBLICATIONS

Patwardhan, A. et al., Selection of Optimum Affinity Tags from a Phage–Displayed Peptide Library: Application to Immobilized Copper(II) Affinity Chromatography, J. Chromat. 787: 91–100 (1997).

Patwardhan, A. et al., Phage–Displayed Libraries for the Selection of Optimal Affinity Peptides for Protein Purification Using Ni–Nitrilotriacetic Acid Chromatography, Biotech. Techniq. 12: 421–424 (1998).

Regan, L., Protein Design: Novel Metal–Binding Sites, TIBS 20: 280–285 (1995).

Silver, S., Bacterial Resistance ATPases: Primary Pumps for Exporting Toxic Cations and Anions, Trends. Biol. Sci. 14: 76–80.

Sousa, C. et al., Metalloadsorption by *Escherichia coli* Cells Displaying Yeast and Mammalian Metallothionens Anchored to the Outer Membrane Protein LamB, J. Bact. 180: 2280–2284 (1998).

Tohoyama, H. et al., Resistance to Cadmium is Under the Control of the CAD2 Gene in the Yeast *Saccharomyces cerevisiae*, Curr Genet. 18: 181–185 (1990).

Waffenschmidt, S. et al., Isodityrosine Cross–Linking Mediates Insolubilization of Cell Walls in Chlamydomonas, Plant Cell 5: 809–820 (1993).

Yoon, K. et al., Regulation of the cadA Cadmium Resistance Determinant of *Staphylococcus aureus* Plasmid pI258, J. Bacteriol. 173: 7636–7649 (1991).

Cai, X. et al., Applications of Eukaryotic Algae for the Removal of Heavy Metals from Water, Molecular Marine Biology and Biotechnology 4: 338–344 (1995).

Cai, X. et al., Heavy Metal Binding Properties of Wild Type and Transgenic Algae (*Chlamydomonas* sp.), New Developments in Marine Biotechnology, 189–192 (1998).

Cai, X. et al., Growth and Heavy Metal Binding Properties of Transgenic Chlamydomonas Expressing a Foreign Metallothionein Gene, Int. J. Phytoremediation 1: 53–65 (1999).

Chaney et al., Phytoremediation of Soil Metals, Current Opinion in Biotechnology, 1997, vol. 8, pp. 279–284.

Misra et al., Heavy Metal Tolerant Transgenic *Brassica napus* L. and *Nicotiana tabacum* L. Plants, Theor. Appl. Genet. 1989, vol. 78, pp. 161–168.

Brown et al., Introduction of Exogenous DNA into *Chlamydomonas reinhardtii* by Electroporation, Molecular and Cellular Biology, 1991, vol. 11, No. 4, pp. 2328–2332.

\* cited by examiner

METHOD OF MAKING MICROALGAL-BASED ANIMAL FOODSTUFF SUPPLEMENTS, MICROALGAL-SUPPLEMENTED ANIMAL FOODSTUFFS AND METHOD OF ANIMAL NUTRITION

TECHNICAL FIELD OF THE INVENTION

The present invention in the field of animal foodstuffs for the delivery of essential metals.

BACKGROUND OF THE INVENTION

The objective of the present invention is to produce a safe, biodegradable trace metal binding system that effectively delivers metals, such as chromium, copper, manganese, selenium and zinc to animals, including livestock such as cattle.

SUMMARY OF THE INVENTION

The present invention generally involves the use of transgenic algae to express metal-specific binding peptides that release bound metals, typically at low pH. As used herein, release at low pH will be understood as meaning release at a pH that occurs somewhere within the digestive tract of the animal fed the foodstuff of the present invention, that pH being lower than that experienced by the foodstuff prior to ingestion by that animal.

The present invention includes an animal foodstuff, a method of producing an animal foodstuff, and a method of providing an animal with nutrition.

In general terms, the invention includes a method of preparing an animal foodstuff composition, the method comprising the steps: (a) providing transgenic algal cells comprising a nucleotide sequence, the nucleotide sequence capable of expressing a non-native metal-binding protein in the transgenic algal cells; (b) binding the metal-binding protein, with at least one metal so as to produce a metal-bound adduct of the metal-binding protein; and (c) admixing the metal-bound adduct with the animal foodstuff.

The transgenic algal cells may be from any strain that may be genetically altered to carry the nucleotide sequence capable of expressing a non-native metal-binding protein. Examples include those selected from the genus *Chlamydomonas*, such as those from the strain *Chlamydomonas reinhardtii* for copper and zinc binding.

The metal-binding protein may be adapted to bind any desired metal or combination of metals, such as those selected from the group consisting of cobalt, chromium, copper, iron, manganese, molybdenum, selenium and zinc, or combinations thereof. An example of a metal-binding protein is chicken Type II Metallothionein.

It is preferred that the transgenic algal cells are in a dried state prior to introduction into the animal foodstuff.

The present invention also includes an animal foodstuff composition comprising: (a) an animal foodstuff; and (b) transgenic algal cells, as described above, expressing a metal-binding protein not found in native algal cells, such that the transgenic algal cells contain the metal-binding protein, the metal-binding protein being bound to a metal.

The foodstuff may be any natural or synthetic foodstuff or feedstock, such as grain or fodder for livestock, commercial pet foods for pet animals, etc.

The present invention also includes a method of providing a dietary metal supplement to an animal, the method comprising feeding to the animal a foodstuff comprising transgenic algal cells expressing a metal-binding protein not found in native algal cells, as described above, such that the transgenic algal cells contain the metal-binding protein, the metal-binding protein being bound to a metal.

With specific regard to copper or and zinc binding, one may determine the copper and zinc binding capacity of transgenic algae expressing metallothioneins. Presently, transgenic algae that express a chicken metallothionein-II gene fused to a plasma membrane protein have been generated. Results indicate that the metallothionein domain is expressed on the surface of the cell and effectively binds metals. Metallothioneins are cysteine-rich proteins that selectively sequester copper, zinc, lead, cadmium, cobalt, nickel, mercury, silver, and gold. Other metals such as calcium and iron do not bind to metallothioneins. Metallothioneins may be sub-divided into three classes based on their primary structures. Class I and II metallothioneins are low molecular weight (10 kD) translationally synthesized proteins, which have multiple CysXCys, or CysCys clusters. Each metallothionein binds 6–7 metal ions via formation of metal-thiolate clusters. The class III metallothioneins or phytochelatins are typically found in plants, algae, and fungi. Phytochelatins are non-translationally synthesized metal-thiolate polypeptides related to glutathione and have the repetitive sequence $(\gamma GluCys)_n Gly$, where n=2–11. The trace metal binding constants are highest for the translationally synthesized metallothioneins (I and II) ($K_3=10^{25.5}$ M$^{-1}$) and are lower for the phytochelatins ($K_3=10^{19}$ M$^{-1}$). Significantly, metallothioneins bind metals with greatest affinity at neutral pH and release metals at low pH (Adhiya et al., *J. Collloid. Interface Sci.*, 1999).

Metallothionein

Metallothionein is a general name given to heavy metal (Cd, Zn, Cu)-binding proteins having similar properties. They typically have low molecular weights, high contents of cysteinyl residues, and bind heavy metals tightly through mercaptide bonds.

Metallothioneins (MTs) were discovered in 1957 when Margoshes and Vallee searched for a tissue component responsible for the natural accumulation of cadmium in mammalian kidney (Margoshes and Vallee 1957). Metallothioneins may be one of the few biological compounds known to specifically bind this metal. However, as documented already in the earliest reports, cadmium is but one of the several metallic components bound by MTs, the others being most commonly zinc and copper. Since the discovery of MTs, intense interest in this small, structurally unique, and functionally enigmatic group of proteins has been driven by its putative roles in cadmium detoxification and essential metal metabolism.

Definition and Occurrence

The first MTs characterized were lower molecular weight, sulfur containing proteins, which consist of a single polypeptide chain of 61 amino acids residues. Twenty of the residues are cysteines, which chelate up to seven bivalent cations, leaving neither free thiol groups nor a disulphide bridge (Kojima, et al., 1976). Typically MTs also lack aromatic amino acids residues. All cysteines in MTs occur in the reduced form and are coordinated to the metal ions through mercaptide bonds, giving rise to spectroscopic features characteristic of metal-thiolate clusters (Martin, et al., 1992).

In view of these unique chemical characteristics, the phenomenological definition was adopted that any polypeptide resembling mammalian MT in several of these features can be named an MT (Fowler et al., 1987).

MTs now have been identified not only in the animal kingdom but also in higher plants, eukaryotic microorganisms, and in some prokaryotes (cited in Hamer 1986, Kagi and Kojima, 1987). To date, all organisms that have been screened contain one or more types of cysteine-rich polypeptides which selectively sequester heavy or soft metals including copper, zinc, lead, cadmium, cobalt, nickel, mercury, silver and gold (Grill et al., 1985; Jackson et al., 1987; Kagi and Schaffer, 1988; Rauser, 1990).

Taking into account structural relationships, they can be subdivided into three classes (Fowler et al., 1987, Furey et al., 1986 Jackson et al., 1987; Rauser, 1990). Class I MTs (MT-I) include mammalian MTs and polypeptides with related primary structure from other phyla. They are characterized by (1) molecular weight of about 10 kD (equivalent to about 60 amino residues), (2) the presence of 20 invariant cysteine (Cys) residues arranged in CysXCys clusters, where X is any amino acid, (3) the absence of aromatic amino acid residues, and (4) the presence of 6–7 metal-thiolate clusters whose number varies with respect to the type of metal bound. Class II MTs (MT-II) are low molecular weight and Cys-rich metal binding proteins, but the distribution of Cys residues does not correspond to that in mammalian MTs. These proteins have been identified in sea urchin, wheat, yeast, and certain prokaryotes (Kagi, 1993). The third class of MTs (MT-III) are nontranslationally synthesized metallothiolate polypeptides related to glutathione and have repetitive sequences: $(\gamma\text{-GluCys})_n\text{Gly}$, where n=2–11 (Rauser, 1990). The MT-IIIs are also known as phytochelatins (PC), and have smaller molecular weights (1–2 kD) than MT-I or MT-IIs. Phytochelatins, as their name implies, are found in plants.

Primary Structure of MTs

Owing to improvements in protein sequencing techniques and the facile determination of nucleotide sequences, primary structure data are now available for some class I MTs, class II MTs and various homologous sets of class III MTs (Rauser, 1990; Kagi, et al., 1988). Table 1 shows some sequences of the three classes of MTs (Kagi, et al., 1988). All class I and class II MTs characterized thus far are single-chain proteins.

Mammalian forms contain 61–62 amino acid residues; chicken MT and sea urchin MTs contain 63–64 residues, respectively. Shorter single chain proteins are found in invertebrates and in certain fungi, the shortest one with 25 residues in *Neurospora crassa* (Lerch, 1980). The basic features of MT structure have been established by chemical and spectroscopic methods. The formation of two distinct metal clusters in rabbit liver MT was first shown by $^{113}$Cd NMR (Otvos, et al., 1980). The seven $Cd^{2+}$ ions are bound in clusters of four and three metals formed by bridging and terminal cysteine thiolate ligands. All 20 cysteines participate in metal binding, and each of the seven metals is tetrahedrally bound. Rat liver MT can be cleaved by trypsin into two domains which bind metals individually in the same way as in the intact protein (Kagi, 1993). The N-terminal a-domain includes residues 1–30, which contain nine cysteines and form a cluster with three Cd or Zn liganded by three bridging and six terminal cysteine ligands; the C-terminal b-domain contains residues 31–61, contains 11 cysteines and forms a cluster with four Cd or Zn liganded by five bridging and six terminal cysteine ligands (FIG. 1). The structure of MT in solution has been studied in detail by two dimensional $^{113}$Cd-$^1$H NMR methods, and also confirmed by X-ray diffraction (Robbin, et al., 1991). Three dimensional structures have been determined for rabbit liver $Cd_7$-MT, rat liver $Cd_7$-MT, and human liver $Cd_7$-MT (Kagi, 1993). These investigations have established the cysteine ligand to metal coordination pattern for the two domain clusters, they all show very similar conformations.

g-Glutamylcysteinylglycones detected in yeast, algae and certain plants are classified as class III MTs, or phytochelatins. The class III MTs are quite different in origin and structure although they show many phenomenological and functional similarities. Like the MTs of the higher organisms they are isolated from the cell cytosol as low-molecular weight, metal rich complexes. They are synthesized by enzymatic reactions rather than on ribosomes. Their structures involve unusual repeating sequences of γ-Glu linkages to cysteine, which produce the general formula: $(\gamma\text{-Glu-Cys})_n\text{Gly}$ (FIG. 2). The n value typically ranges from 2–8 or higher and sometimes Gly is replaced by b-Ala, Ser or Glu.

TABLE 1

Classification of Metallothioneins and Amino Acid Sequences of Representative Forms.

Class I

| | |
|---|---|
| Human | MDP-NCSCAAGDSCTCAGS CKCKECTKCTS CKKSCCSCCBVG-CAKCAQGCI -CKJACD KCSCCA |
| Chicken | MDPQDCTCAAGGSCSCAGS CKCKMCR -CRSCRKSCCSCCPAG-CNNCAKGCVCKEPASSKCSCCH |
| Trout | MDP--CECSKTGS CNCGGSCKCSN CA -CTSCKKS CCPCCPSD -CK- CASGCVCKGKTC DTS CCQ |
| Crab | PDP---C-C--NDKCDSKEGECKTG-CK- CTSCRCPPCEQCSSG--C K-CANKEGCRKTCSKPCSCCP |
| N. crassa | --GDCGC SGASS-- CNCGSG -CS---CSMCGSK |

Class II

| | |
|---|---|
| Sea urchin | MPDVKCVCCTEGKECACFGQDCCVTGECCKDGTCCGICINAACKCANGCKCGSGCSCTEGNCA |
| Yeast | QNEGHECQCQCGSCKMNEQCKKSCSCPTGCNSDDKCPCGMKCEETKKSCCSGK |
| Wheat | GCNDKCGCAVPCPGGTGCRCTSARCGAAAGEHTTCGCGEHCGGNPCACGGGEGTPSGCAN |
| Synechocystis | TSTTLVKCACEPCLCNVDPSKAIDRNGLYYCCEACADGHTGGKGCGHTGCNC |

Class III

| | |
|---|---|
| S. pombe | ECECECG |
| R. canina | ECECECECECECECG |
| P. vulgaris | ECECECECECECEC-b-alanine |

The major sources of peptides for structural analysis have been Cd-binding complexes from *S. pombe* and various plants, particularly tissue culture cells (Rauser 1993). The structure of $(\gamma\text{-EC})_n G$ peptide was confirmed by chemical synthesis of penta-and heptapepides (Kondo et al., 1985) and the nanopeptide (Grill et al., 1985). The recurrent γ-carboxyamide linkage prevented exclusive use of Edman protein sequencing methodology. Steffens et al., (1986) confirmed the sequence of the hepta- and nanopeptides from tomato (*Lycopersicon esculentum*) by mass spectrometry. Enzymatic digestion provided the sequence information of peptides from *Datura innoxia*, the γ-glutamyl linkages were identified by $^{113}$Cd-NMR spectroscopy (Jackson et al., 1987). Using Cd as the inducing metal, the presence of these peptides $(\gamma\text{-EC})_n G$ was tested in three dicotyledonous plants, the alga *Chlorella fusca*, and other species (Gekeler et al., 1988). A small amount of $(g\text{-EC})_2 G$ occurred in *Neurospora crassa*. The n=2 to 6 peptides were also detected in six species of *Basidiomycetes* and four species of *Schizosaccharomyces* in addition to *S. pombe*.

The three classes of MTs are different in their affinities for heavy metals. The binding constants for cadmium range from $K_3=10^{25.5}$ M$^{-1}$ for equine MT-I to $K_3=10^{19}$ M$^{-1}$ for tobacco MT-II (Rauser, 1990). Another measure of metal binding affinity is the pH at which 50% of the bound metal is released from the protein. The higher the affinity for the metal, the lower the pH that is necessary to displace the metal from the protein. Typically, metal ions are displaced from MTs at pH values ranging from 2.0–4.5, with copper and cadmium generally being released at lower pH values. The Cd-MT from cabbage lost half its Cd at pH 4.4 (Wagner, 1984), the complex from tobacco did so at pH 5–5.8, whereas Cd-MT from rat liver dissociated by 50% at pH 3 (Reese, 1987). Kagi and Vallee (1988) found pH values of 3 and 4.5 for Cd and Zn dissociation, respectively, for equine Cd, Zn-MT. The pH-dependent selective release of heavy metals can also be used to selectively harvest heavy metals that vary with respect to their binding constants (Kagi and Schaffer, 1988; Rauser, 1990).

Biological Functions

Metallothioneins are an unusual group of proteins or polypeptides, which have challenged the interest of chemists and life scientists alike for over 30 years. In spite of the rich information on its structure, MT is a protein in search of functions (Karin 1985). More than three decades after the discovery of MT, its functional significance remains a topic of discussion (Karin, 1985: Bremner, 1987). Questions remain with respect to how cadmium exerts its toxicity and its mechanism for exercising its defensive action. The conservation of the structure, the ubiquitous occurrence, and the programmed synthesis of MT in regeneration and development are strong arguments for its playing a crucial role in some fundamental metal-related cell biological process. The main hypotheses thus far considered are that: (1) MT serves as a relatively non-specified metal-buffering ligand to either sequester or dispense metal ions, or (2) it has a specialized function in normal cellular metabolism or development (Kagi and Schaffer, 1988). It may also serve a number of different biological purposes.

That MT is the cellular component responsible for much of the intracellular sequestration of Cd, bringing about the long biological half-life of this nonessential element, is unquestioned (Webb, 1987a). Through gene amplification (Griffith et al., 1983, Durnam and Palmiter 1987) and transfer (Thiele et al. 1986, Ecker et al. 1986) experiments, the presence of MT is shown to be strongly associated with Cd detoxification. In cultured mammalian cell lines stable resistance to Cd can be brought about by massive amplification of the MT genes (Beach, et al., 1981). However, the production of excessive amounts of Cd-containing MT has been suggested as a causative factor in bringing about kidney damage in chronic Cd poisoning (Nordberg, et al., 1987), thus causing doubt on the biological importance of MT synthesis as a specific and effective Cd defense mechanism in animals. MTs have also been implicated in the sequestration of other nonessential metals, such as Hg, Ag, Au, Pt and Pb (Webb, et al., 1987a). Such effects have been claimed to be responsible for the development of resistance toward Au- and Pt-containing drugs in cultured cells and the selective protection of some tissue from such agents in animals following preinduction of MT (Naganuma et al., 1987; Monia at al., 1987).

Hypersensitivity to elevated trace-metal concentrations has also been observed in fungal (Hamer, 1986) and prokaryotic (Turner, et. al., 1993) cells with deleted MT genes, selected for enhanced tolerance to certain trace metal ions. *Saccharomyces cerevisiae* cells lacking the MT gene (CUP1) have normal cell growth, differentiation, and copper metabolism. These mutants grow with normal doubling times in standard, low-copper media, and are capable of mating, diplophase growth, germination and accumulation of copper (cited in Hamer, 1986). CUP1-deficient cells are, however, hypersensitive to elevated concentrations of copper. Sequestration of excess copper may be an exclusive role of MT in *Saccharomyces cerevisiae*.

The preponderance of Zn in most MT preparations and the responsiveness of MT-bound Zn and Cu to the dietary supplies of these essential nutrients suggest a role in their metabolism and have led to a large number of studies (cited in Bremner 1987). As a homeostatic mediator, MT could donate metal ions in the biosynthesis of Zn and Cu-containing metalloenzymes and metalloproteins (Brady, 1982). The emergence of Cu-MT in *N. Crassa* prior to the formation of the Cu-containing enzymes would be in concert with such a role (Huber et al., 1987), as are in vitro experiments which have demonstrated that Cu and Zn can be transferred from MT to the apo forms of a number of Cu and Zn proteins (Beltramini, et al, 1982, Brady, 1982). Conversely, when Cu and Zn accumulated intracellularly, the reactive ions can be sequestered in a chemically innocuous form by binding to newly synthesized apoMT. This mechanism is believed to account for the accumulation of large amounts of Cu-MT in tissues and cells of organisms affected with an inherited disorder of Cu metabolism (Sternlieb, 1987). Protection from the effects of excessive ionic Cu by sequestration is thus far the only documented benefit of MT induction in yeast (Thiele, et al., 1986; Ecker et al., 1986), *N. Crassa* (Lerch et al., 1980), and in copper-resistant forms of *Agrostis gigantea* (Rauser, et al., 1980).

A biological role, probably unrelated to a detoxification function for metals, is suggested by the fact that in certain tissues and cell types MT is induced by chemical and physical stress. These effects, which are most prominent in liver and mediated in part by hormones, resemble an acute phase response (Bremner, 1987). In some cases, such as in the exposure to electrophilic agents, i.e., $O_2$, free radicals, and alkylating agents, the increased supply of MT could provide neutralizing nucleophilic equivalents. However, in most other instances it is unclear how the organism benefits from increased MT biosynthesis.

One possibility is that MTs may have metalloregulation function in cellular repair processes, growth, and differentiation. This was first suggested by the parallelism of enhanced RNA synthesis with increased Zn-MT formation observed in the liver of rats recovering from partial hepatectomy (Ohtake et al., 1978) and is supported by the programmed regulation of MT mRNA and protein levels during embryogenesis (Nemer et al., 1984) and at different stages of fetal and prenatal development (Andrews, et al., 1984). In view of the known effects of Zn on embryogenesis, its participation in RNA polymerases and its serving as a structural modulator of the Zn finger domain in several DNA-binding proteins, it is tempting to hypothesize that Zn-MT plays a part in expression of genetic information.

TABLE 2

Factors that Induce Metallothionein Synthesis in Cultured or in vivo Animal Cells.

| | |
|---|---|
| metal ions: Cd, Zn, Cu, Hg, Au, Ag, Co, Ni, Bi. | Streptozotocin |
| | 2-propanol |
| glucocorticoids | ethanol |
| progesterone | ethionine |
| nitrogen | alkylating agents |
| glucagon | chloroform |
| catecholamines | starvation |
| interleukin I | infection |
| interferon | physical stress |
| endotoxin | X-irradiation |
| dextran | high $O_2$ tesion | for citations, see Palmiter (1987) and Bremner (1987).

Molecular Biology of MTs

While all plants examined to data contain phytochelatins, apparently, only a few contain class I and class II MTs. An MT-I has been identified in immature embryos of wheat and MT-I has been identified in barley, pea, *Mimmulus* sp., *Synechoccocus*.sp., maize, and soybean (de Miranda et al., 1990; Kawashima et al., 1991, 1992; Lindow et al., 1989; Reese & Wager, 1987; Robinson et al., 1992; Shimizu et al. 1992; Steffens et al., 1986). During the past years, different MT cDNAs have been cloned from eukaryotic cells (Giffith, et al., 1983; Peterson et al., 1984; Schmidt and Hamer, 1983; Thiele et al., 1986). Genes encoding MTs from one organism have also been transferred and expressed in other organisms. Plant and animal class I and II MTs have been expressed in *E. coli* and in transgenic plants (tobacco, *Brassica campestris* and *Arabidopsis thaliana*, Evans et al., 1992; Lefebvre et al., 1987; Maiti et al., 1989, Odawara et al., 1995). Significantly, the expression of foreign MTs increased the heavy metal binding capacity of each host. *E. coli* cells expressing human MT-I fusion proteins bound 66-fold more Cd than non-MT-I expressing cells and accumulated 90% of the total Cd present in the medium (2.0 uM Cd in medium) (Jacobs et al., 1989). Transgenic *Brassica campestris* plants expressing the Chinese hamster MT-II had a four-fold increase in Cd binding capacity (Lefebvre et al., 1987). Furthermore all the Cd in the plants (grown in 1.0 mM Cd) was bound to MT-II. Similar studies with transgenic tobacco and *Arabidopsis* plants expressing either a mouse or pea MT-II, respectively, demonstrated that transgenic plants had a higher resistance to Cd poisoning (Evens et al., 1992; Maiti et al; 1989). While these studies indicate that expression of class I and II MTs in transgenic organisms can increase their heavy metal binding capacity, there is evidence that elevated expression of phytochelatin (class III MTs) does not increase heavy metal tolerance (Harmens et al., 1993). As indicated earlier, the heavy metal binding constant of phytochelatins is seven orders of magnitude lower than those of class I and II MTs. These results indicate that the expression of higher binding affinity MTs (class I and II) is likely to increase heavy metal binding capacity unlike the expression of phytochelatins.

DETAILED DESCRIPTION OF THE PREFERRED EMBODIMENT(S)

Figure 1:
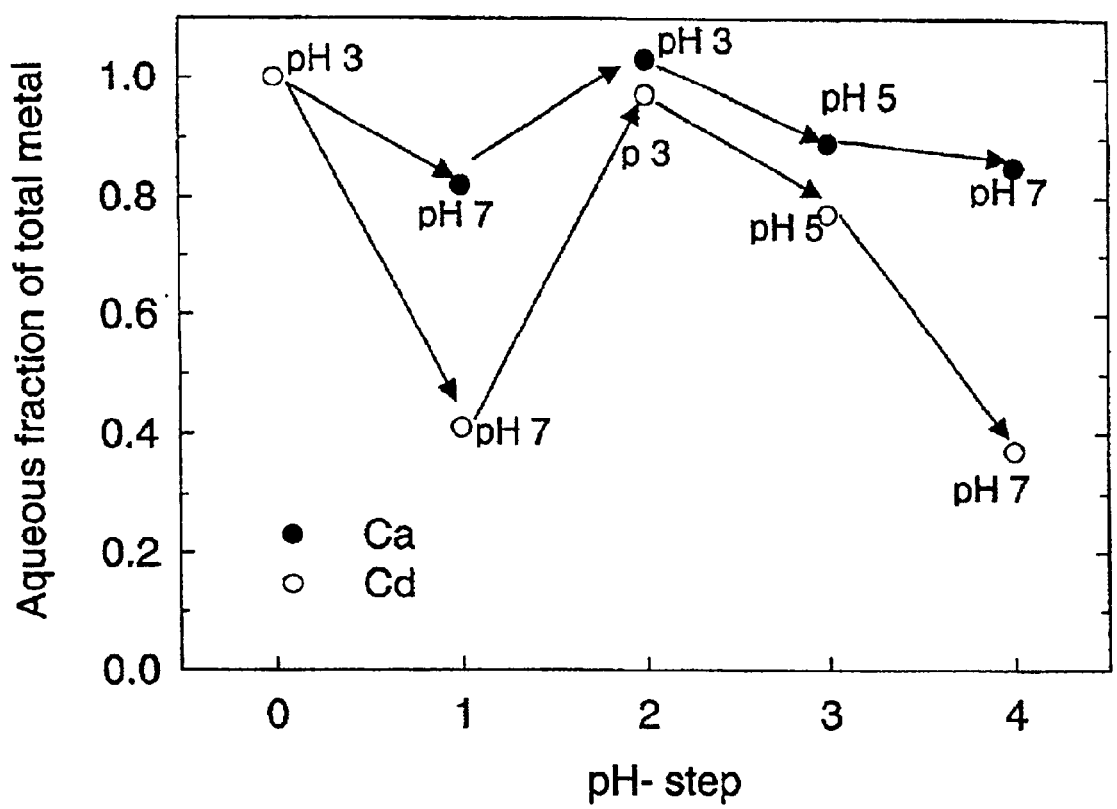
FIG. 1 is a graph that shows the adsorption and desorption of cadmium from freeze-dried *Chlamydomonas* as a function of pH, according to one embodiment of the present invention.

In accordance with the foregoing summary, the following presents a detailed description of the preferred embodiment of the invention that is currently considered to be the best mode.

The copper and zinc binding capacity of the transgenic algae expressing metallothionein may be determined and quantified prior to the production of the animal foodstuff of the present invention. Metal binding may be quantified by ICP-mass spectrometry and replicate experiments may be carried out to determine statistical significance. Titration of pH-dependent metal binding using both live and dead cells may also be done in order to determine the preferred candidate(s), depending upon the desired application. An example of the pH-dependent binding of cadmium treated cells is shown in FIG. 1. Note that calcium does not exhibit a pH-dependent binding to *Chlamydomonas* cell walls and that the cadmium binding at pH 8.0 is nearly 95%.

Studies indicate that there are cadmium-specific binding sites on the cell surfaces of *Chlamydomonas* that release cadmium in a pH-dependent manner. These sites tolerate high temperature treatments (300° C.) and may be regenerated multiple times (>20x) with little effect on metal binding capacity. It is expected that metallothionein will have a similar behavior.

Unique metal-binding peptides (MBP) that sequester specific trace metals (chromium, copper, manganese, selenium and zinc) with high affinity and in a pH dependent manner may be identified. These MBPs may be expressed on the cell surface of *Chlamydomonas* cells as fusion proteins or otherwise in or on other cells. MBPs also may ill be transformed into transgenic *Chlamydomonas* expressing the MT-II, P5CS and RHL genes. These genes increase the trace metal binding capacity and tolerance of live algae. In this way, the determination as to whether the expression of a variety of different metal binding proteins increases the overall trace metal binding capacity of the cells may be made. The selectivity and capacity of trace metal binding of the cells may increase by at least an order of magnitude over current levels. Accordingly, the present invention may involve the expression of more than one normative gene to allow or enhance metal binding.

The Identification of Oligopeptides that Selectively Bind Trace Metals

A variety of strategies have been developed to identify MBPs. Metal-binding domains have been identified in naturally occurring metallo-proteins (such as metallothioneins and trace metal chaperoning) by structural and functional analysis using chemical modification, site-directed mutagenesis, NMR, and crystallographic approaches (Brown, S., *Nature Biotechnology,* 1997, (15), 269–271: Goud, G. N. et al., *Int. J. Biol. Chem.,* 1997, (3), 123–136; Harford, C. and Sarkar, B., *Acc. Chem. Res.,* 1997, (30), 123–130; Kotrba, P. et al., *Applied and Environmental Microbiology,* 1999, (65), 1092–1098; Patwardhan, A. V. et al., *J. Chromat.,* 1997, (787), 91–100; Patwardhan, A. V. et al., *Biotech. Techniq.,* 1998, (12), 421–424). Some examples of trace metal binding domains that have been identified in metallo-proteins include the metal-binding domains of metallothioneins, the metal binding domains of metal pumps, and the metal binding domains of chaperoning, e.g. the cadABC, the czcABCD genes Nucifora, G. et al., *Proc. Nat. Acad. Sci.,* 1989, (86), 3544–3548; Silver, S. et al., *Trends. Biol. Sci.,* 1989, (14), 76–80; Tohoyama, H. et al., *Curr. Genet.,* 1990, (18), 181–185; Yoon, K. and Silver, S., *J. Bacteriol.,* 1991, (173), 7636–7642; Yoon, K. et al., *J. Bacteriol.,* 1991, (173), 7643–7649). While these biochemical strategies are effective they may be time consuming.

A more rapid approach for identification of MBPs involves screening combinatorial DNA or oligopeptide libraries in phages which display potential MBPs on the surface of the coat protein (Kotrba, P. et al., *Applied and Environmental Microbiology,* 1999, (65), 1092–1098; Patwardhan, A. V. et al., *J. Chromat.,* 1997, (787), 91–100; Patwardhan, A. V. et al., Biotech. Techniq., 1998, (12), 421–424). Combinatorial DNA libraries are commercially available and may be used to "biopan" for MBPs that recognize specific trace metals. These combinatorial libraries contain all possible codon combinations encoding polypeptides of a specific length. For example, a combinatorial library encoding all possible combinations of randomized heptapeptides would have $20^7$ or $2.8 \times 10^9$ possible amino acid combinations. One example of such a library is that available from New England Biolabs (NEB). The NEB combinatorial phage library contains small, randomized oligonucleotides fused near the 5' end of the pill gene of the bacteriophage M13. The pill gene encodes the minor coat protein of the M13 phage. The inserted oligonucleotides are located just downstream of the pill signal peptide cleavage site so that following proteolytic processing the randomized heptamer is exposed at the N-terminus of the pill protein. A short spacer (encoding Gly-Gly-Gly-Ser-pIII protein) that is fused then follows the randomized heptapeptide to the pIII gene. This spacer facilitates exposure of the heptapeptide on the phage surface. This spacer also allows free rotation around the α-carbon atom so as not to reduce steric constraints on the folding of the heptamer (Regan, L., 1995). Using similar combinatorial libraries several investigators have successfully "biopanned" for MBPs (Kotrba, P. et al., *Applied and Environmental Microbiology,* 1999, (65), 1092–1098; Patwardhan, A. V. et al., *J. Chromat.,* 1997, (787), 91–100; Patwardhan, A. V. et al., *Biotech. Techniq.,* 1998, (12), 421–424). To biopan for MBPs the metal of interest is immobilized on a gel matrix by coordination to a metal ligand, typically nitriloacetic acid (NTA) or iminodiacetic acid (IDA), which is covalently bound to the resin. The phage library then is batch-mixed with the immobilized metal matrix and the non-specifically bound phages are washed from the matrix under defined conditions of ionic strength and pH shifts (neutral→acid). This process is repeated multiple times to enrich for phage having MBPs. The MBPs then may selectively removed from the immobilized metal matrix either by addition of metal (high concentrations) to the wash buffer, by addition of a metal chelator (EDTA or imidazole), or by a shift in pH (preferred for this application). Following several rounds of purification the phage displaying MBPs are chromatographed over the same immobilized metal column material, washed, and eluted under defined conditions. The DNA sequence of the metal binding heptapeptide then is determined using pill specific oligonucleotide primers. Since these sequences are short the genes may be artificially synthesized. In addition, convenient restriction endonuclease sites may be incorporated for ligation to some gene of interest to produce a fusion protein. Another potentially useful modification would be to synthesize MBP tandem repeats (+/−spacer regions, e.g. Gly-Gly) or different combinations of MBPs to enhance or diversify the metal binding properties of the MBP-fusion protein. Using this strategy a variety of MBPs have been identified that bind gold, copper, nickel, chromium and other metals (Kotrba, P. et al., *Applied and Environmental Microbiology,* 1999, (65), 1092–1098; Patwardhan, A. V. et al., *J. Chromat.,* 1997, (787), 91–100; Patwardhan, A. V. et al., *Biotech. Techniq.,* 1998, (12), 421–424). In addition, MBPs have been identified that have superior binding properties to nickel affinity chromatography matrices relative to the hexa-His MBP that is frequently used as a fusion peptide tag for protein purification (Patwardhan, A. V. et al., *Biotech. Techniq.,* 1998, (12), 421–424). Some MBP sequences that have been identified include:

| Metal | Metal Binding Peptides |
|---|---|
| Nickel | HHHHHH, WHHHPH, AQHHHH, CAIH, GGH |
| Copper | HHHHHH, SPHHGG, HHHMVH, AMLKLH |
| Chromium | QHQK |
| Gold | MHGKTQATSGTIQS |

Using the New England Biolabs Ph.D. 7 (heptamer) combinatorial phage library MBPs using copper- and lead-IDA resins have been screened for. Copper and lead specific MPB-phages were eluted by a pH shift from 7.0 to 4.0. Ten MBP-phages that bind to lead-IDA columns and ten MBP-phages that bind to a copper-IDA column have been purified. The determination of the DNA sequence of the region encoding the heptamers may be made. The translated protein sequences then may be compared to each other and protein data banks to determine if there is a consensus domain. Previously identified MBP sequences as well as biopan for chromium, copper, manganese, selenium and zinc binding phages using techniques currently in use may be exploited. Many novel MBPs as well as MBPs that are most compatible as protein fusions with *Chlamydomonas* cell wall and membrane proteins may be identified.

Characterization of Trace Metal Binding Properties of Oligopeptides and Their Tandem Repeats Following identification of the MBPs determination as to the metal binding constants (affinities) of the MBP-phages by equilibrium dialysis may be made (Adhiya et al., *J. Colloid. Interface Sci.,* 1999). Known titers of MBP-phage as well as control phage (M13 phage with no insert in the pill gene) may be dialyzed against various concentrations of trace metals in a defined medium until metal-binding to the phage has reached equilibrium (determined empirically). Various components of the dialysis media may be altered to determine their effects on metal binding. Some of the factors that may be varied include pH (using non-complexing buffers), ionic strength, concentrations of potentially competing metals, and temperature. Atomic absorption or ICP-mass spectrometry using routine procedures used in the lab (Adhiya et al., J. Colloid will determine the amount and identity of the metal bound to the phage. *Interface Sci.,* 1999). The objective is to identify the most promising MBPs for construction of *Chlamydomonas* protein fusions. Identification of MBPs with varying binding affinities and specificities for different metals may be made.

Expression of Trace Metal Binding Oligopeptides on *Chlamydomonas* Cells

Some possible gene (protein) fusion constructs would include the relevant MBPs listed in the table fused to the N-terminal and C-terminal domain regions of the *Chlamy-*

*domonas* genes encoding hydroxy-proline rich cell wall proteins (Adair, W. S. and Apt, K. E., 1990; Waffenschmidt, S. et al., *Plant Cell,* 1993, (5), 809–820). The N- and C-terminal domains of the cell wall proteins are charged and lack the proline and tyrosine residues which are presumably involved in proper folding and cross-linking (isodityrosyl) of the cell wall proteins (Adair, W. S. and Apt, K. E., 1990; Waffenschmidt, S. et al., *Plant Cell,* 1993, (5), 809–820). Thus, the addition of foreign MBP domains to the termini of the cell wall proteins will reduce the likelihood that they will disrupt the cell wall structural protein. Furthermore, since MBPs are short in length the likelihood of the metal-binding domains disrupting the structural integrity of the fusion partner is low. It is possible, however, that the metal binding domain cell-wall fusion proteins may be non-functional or that one or more fusions may interfere with protein targeting to the cell wall or be deleted as part of a targeting sequence. Therefore, fusion of the metal-binding domains to the N- and C-terminus of the $CO_2$ induced membrane protein (NIH-Genbank accession number CRU31976) described by Moroney and colleagues will take place. The MBP-protein fusions all may be made using glycine-glycine junctions to facilitate the independent and proper folding of the metal binding domain (MBD). Since the MBP proteins may be fused to *Chlamydomonas* proteins it is also less likely that there may be expression problems than if they were fused to a foreign protein.

All gene fusion constructs may be introduced into *Chlamydomonas* using the aforementioned high-expression integrative vector, pSSCR7, or its derivatives having selectable marker genes. *Chlamydomonas* transformants may be verified by PCR and Southern blot analysis and the expression of the fusion protein may be determined by northern blot analysis. Generation of antibodies against the native *Chlamydomonas* proteins used for the fusions to determine the abundance of the MBP-fusion protein in transformed *Chlamydomonas* will take place. The fusion proteins may be identified by western blot analysis of SDS-PAGE separated proteins. Fusion proteins may be quantified on the basis of their abundance relative to that of the non-fusion protein in transformed and in wild type algae. It is noted that the size of the heptapeptide-fusion protein should be 800 Dalton greater than the native protein and thus be distinguishable from the native protein on the western blot. It is expected that the fusion proteins will not vary greatly in their level of expression and may be expressed at high levels when using the pSSCR7 vector.

Following verification of the expression of the MBP-fusion proteins, *Chlamydomonas* cells may be harvested and determination as to their metal binding capacity may be made. The affinity and selectivity of each transformant and wild type for the five different metals (chromium, copper, manganese, selenium and zinc) may be determined (Adhiya et al., *J. Collloid. Interface Sci.,* 1999). In addition, determination as to whether pH has an effect on the binding of specific metals may be made. As previously mentioned, the ability to selectively absorb and desorb heavy metals as a function of pH allows us to recycle the dried cells multiple times and use them essentially as an ion-specific exchange resin (FIG. 1). Release of genetically modified organisms will not be an issue of concern because the cells are dead. The transgenic material may have enhanced binding affinity and capacity relative to wild type.

The possibility of introducing multiple metal-binding domains into a single gene fusion as tandem repeats (separated by spacer regions (Gly-Gly)) may be explored. It has been observed that tandem repeat MBP constructs may not enhance metal binding, however (Kotrba, P. et al., *Applied and Environmental Microbiology,* 1999, (65), 1092–1098). Therefore, the metal binding properties of repetitive MBD peptides may be characterized by expressing the constructs in the M13 phage system and by determining the metal-binding capacity and affinity by equilibrium dialysis (as described above).

Since the MBDs are small these constructs should not interfere with proper targeting and folding of *Chlamydomonas* fusion proteins. Similar to the procedures described above, these polymeric MBD gene fusions may be transformed and expressed in *Chlamydomonas*. It is expected that some MBD polymers will enhance metal binding in phage and *Chlamydomonas* and that other MBD polymers will not enhance metal binding.

Gene constructs encoding trace metal binding factors also may be integrated into the genomes of wild type as well as transgenic *Chlamydomonas* cells expressing MT, P5CS, and/or the RHL gene products. It is predicted that expression of MBPs on the surface of *Chlamydomonas* may enhance the metal-binding capacity of live cells more than dead cells since the MBPs may facilitate transfer of metals from the bulk medium to the cytoplasm (Yoon, K. et al., *J. Bacteriol.,* 1991, (173), 7643–7649). The determination as to the metal-binding capacity of live cells expressing MBP-fusion proteins using techniques commonly used may be made (see Cai et al., 1995–98). *Chlamydomonas* transformants expressing novel proteins in their cytoplasm have been generated that may have enhanced trace metal binding capacities. The MBP-fusion proteins may be introduced into these transformants or host strains using the pSSCR7 vector containing a unique selectable marker gene. Transformants may be verified as above and metal binding capacity and tolerance may be determined relative to wild type and the host strain using standard protocols (Cai, X-H. et al., *Int. J. Phytoremediation,* 1999, (1), 53–65). The expression of the MBP-protein fusion will act as a "magnet" to facilitate diffusion of metal from the medium to the cytoplasm and therefore increase the metal-binding capacity of the host strain (Kotrba, P. et al., *Applied and Environmental Microbiology,* 1999, (65), 1092–1098; Sousa, C. et al., *J. Bact.,* 1998, (180), 2280–2284).

Once the transgenic algae have been identified that bind each of the target metals in a pH-dependent manner they may be provided for field testing studies in cattle.

The preferred embodiments herein disclosed are not intended to be exhaustive or to unnecessarily limit the scope of the invention. The preferred embodiments were chosen and described in order to explain the principles of the present invention so that others skilled in the art may practice the invention. Having shown and described preferred embodiments of the present invention, it will be within the ability of one of ordinary skill in the art to make alterations or modifications to the present invention, such as through the substitution of equivalent materials or structural arrangements, or through the use of equivalent process steps, so as to be able to practice the present invention without departing from its spirit as reflected in the appended claims, the text and teaching of which are hereby incorporated by reference herein. It is the intention, therefore, to limit the invention only as indicated by the scope of the claims and equivalents thereof.

What is claimed is:

1. A method of preparing an animal foodstuff composition, said method comprising the steps:
   (a) providing transgenic algal cells comprising a nucleotide sequence, said nucleotide sequence capable of expressing a non-native metal-binding protein in said transgenic algal cells;

(b) binding said metal-binding protein with at least one metal so as to produce a metal-bound adduct of said metal-binding protein; and (c) admixing said metal-bound adduct with said animal foodstuff.

2. A method according to claim 1 wherein said transgenic algal cells are from the genus *Chlamydomonas*.

3. A method according to claim 1 wherein said transgenic algal cells are from the strain *Chlamydomonas reinhardtii*.

4. A method according to claim 1 wherein said metal-binding protein is adapted to bind a metal selected from the group consisting of chromium, cobalt, copper, iron, manganese, molybdenum, selenium and zinc, and mixtures thereof.

5. A method according to claim 1 wherein said metal-binding protein is chicken Type II Metallothionein.

6. A method according to claim 1 wherein said transgenic algal cells are in a dried state prior to introduction into said animal foodstuff.

7. An animal foodstuff composition comprising:

a) an animal foodstuff; and b) transgenic algal cells expressing a non-native metal-binding protein in said transgenic algal cells, such that said transgenic algal cells contain said metal-binding protein, said metal-binding protein being bound to a metal.

8. An animal foodstuff composition of claim 7, wherein said metal-binding protein is bound to a metal selected from the group consisting of chromium, cobalt, copper, iron, manganese, molybdenum, selenium and zinc, and mixtures thereof.

9. The animal foodstuff composition of claim 7 wherein said transgenic algal cells are of the genus *Chlamydomonas*.

10. An animal foodstuff composition according to claim 7 wherein said transgenic algal cells are of the strain *Chlamydomonas reinhardtii*.

11. An animal foodstuff composition according to claim 7 wherein said metal-binding protein is chicken Type II Metallothionein.

12. An animal foodstuff composition according to claim 7 wherein said transgenic algal cells are in a dried state prior to introduction into said animal foodstuff.

13. A method of providing a dietary metal supplement to an animal, said method comprising feeding to said animal a food stuff comprising transgenic algal cells expressing a non-native metal-binding protein, such that said transgenic algal cells contain said metal-binding protein, said metal-binding protein being bound to a metal.

* * * * *

UNITED STATES PATENT AND TRADEMARK OFFICE
CERTIFICATE OF CORRECTION

PATENT NO. : 6,932,980 B1
DATED : August 23, 2005
INVENTOR(S) : Sayre et al.

It is certified that error appears in the above-identified patent and that said Letters Patent is hereby corrected as shown below:

Title page,
Item [56], References Cited, OTHER PUBLICATIONS, delete
"Harford, C. et al., Amino Terminal Cu(II)- and Ni(II)-Binding (ACTCUN) Motif of Proteins and Peptides: Metal Binding, DNA Cleavage, and Other Properties, Acc. Chem." and insert
-- HARFORD, C. et al., Amino Terminal Cu(II)- and Ni(II)-Binding (ACTCUN) Motif of Proteins and Peptides: Metal Binding, DNA Cleavage, and Other Properties, Acc. Chem. Res. 30: 123-130 (1997). --.
delete "Sousa. C. et al., Metalloadsorption by Escherichia coli Cells Displaying Yeast and Mammalian Metallothionens Anchored to the Outer Membrane Protein LamB, J. Bact. 180: 2280-2284 (1998)." and insert -- SOUSA, C. et al., Metalloadsorption by Escherichia Coli Cells Displaying Yeast and Mammalian Metallothioneins Anchored to the Outer Membrane Protein LamB, J. Bact. 180: 2280-2284 (1998). --.

Column 8,
Line 57, delete "chaperoning" and insert -- chaperonins --.

Column 9,
Line 3, delete "chaperoning" and insert -- chaperonins --.
Lines 31, 33 and 62, delete "pill" and insert -- plll --.
Line 47, delete "nitriloacetic" and insert -- nitrilo-acetic --.

Column 10,
Line 47, delete "pill" and insert -- plll --.

Signed and Sealed this

Seventh Day of February, 2006

JON W. DUDAS
*Director of the United States Patent and Trademark Office*